US011243688B1

(12) United States Patent
Remy et al.

(10) Patent No.: US 11,243,688 B1
(45) Date of Patent: Feb. 8, 2022

(54) BI-DIRECTIONAL APPLICATION SWITCHING WITH CONTEXTUAL AWARENESS

(71) Applicant: Mobile Heartbeat, LLC, Waltham, MA (US)

(72) Inventors: Ron Remy, Waltham, MA (US); Sajikumar Aravind, Burlington, MA (US)

(73) Assignee: Mobile Heartbeat, LLC, Waltham, MA (US)

(*) Notice: Subject to any disclaimer, the term of this patent is extended or adjusted under 35 U.S.C. 154(b) by 0 days.

(21) Appl. No.: 16/704,922

(22) Filed: Dec. 5, 2019

Related U.S. Application Data

(60) Provisional application No. 62/775,715, filed on Dec. 5, 2018.

(51) Int. Cl.
*G06F 3/0488* (2013.01)
*H04W 12/06* (2021.01)
*H04L 29/06* (2006.01)
*G16H 10/60* (2018.01)
*H04M 1/72403* (2021.01)

(52) U.S. Cl.
CPC ......... *G06F 3/04886* (2013.01); *G16H 10/60* (2018.01); *H04L 63/0815* (2013.01); *H04M 1/72403* (2021.01); *H04W 12/06* (2013.01)

(58) Field of Classification Search
None
See application file for complete search history.

(56) References Cited

U.S. PATENT DOCUMENTS

| 8,438,245 | B2* | 5/2013 | Chor | G06F 16/9554 |
| | | | | 709/219 |
| 9,256,462 | B2* | 2/2016 | Hartz | G06F 9/4843 |
| 9,397,995 | B2* | 7/2016 | Sakamoto | H04L 63/168 |
| 10,423,691 | B1* | 9/2019 | Patel | G06F 40/134 |
| 2011/0257989 | A1* | 10/2011 | Kumar | G16H 20/10 |
| | | | | 705/2 |

(Continued)

OTHER PUBLICATIONS

Mobile Heartbeat Clinical Communications web page. Available to the public on Mar. 16, 2016. Retrieved via Internet Archive from [http://www.mobileheartbeat.com/] on [Aug. 12, 2020], 2 pages (Year: 2016).*
Mobile Heartbeat Resources web page. Available to the public on Jun. 6, 2017. Retrieved via Internet Archive from [http://www.mobileheartbeat.com/resources/] on [Aug. 12, 2020], 6 pages (Year: 2017).*

(Continued)

*Primary Examiner* — Amy M Levy
(74) *Attorney, Agent, or Firm* — Kilpatrick Townsend & Stockton, LLP

(57) ABSTRACT

An option within a first application is provided that enables automated switching to a second application. When the option, which is referred to as switching selector, is selected, contextual information (e.g., identification of dependent user, identification of provider, credentials, etc.) about the experience in the first application is gathered and shared with an application switching service. The application switching service generates an identifier that can be used by the mobile device to load a second experience in the second application that is contextually similar to the first experience. This can include automatically logging the user in to the second application and loading dependent user data in the second application associated with the same dependent user that was being viewed in the first application.

18 Claims, 14 Drawing Sheets

(56) References Cited

U.S. PATENT DOCUMENTS

| | | | | |
|---|---|---|---|---|
| 2013/0065569 | A1* | 3/2013 | Leipzig | H04W 8/22 455/416 |
| 2013/0074171 | A1* | 3/2013 | Mark | G16H 10/60 726/7 |
| 2014/0143434 | A1* | 5/2014 | Sanche | H04L 65/4015 709/228 |
| 2015/0248230 | A1* | 9/2015 | Mark | H04L 67/10 715/747 |
| 2015/0278448 | A1* | 10/2015 | Weegar, Jr. | G06F 19/321 707/622 |
| 2015/0347770 | A1* | 12/2015 | Whalley | G06F 21/6245 726/30 |
| 2015/0348126 | A1* | 12/2015 | Baiya | H04L 51/24 705/14.61 |
| 2015/0363774 | A1* | 12/2015 | Priebatsch | G06Q 20/38215 705/75 |
| 2016/0142859 | A1* | 5/2016 | Molinet | H04L 67/42 709/203 |
| 2017/0116161 | A1* | 4/2017 | Stein | G06F 3/04842 |
| 2017/0185248 | A1* | 6/2017 | Lee | G06F 3/04883 |
| 2017/0286614 | A1* | 10/2017 | Morris | A61B 5/14532 |
| 2017/0302725 | A1* | 10/2017 | Carr | G06F 16/256 |
| 2018/0205715 | A1* | 7/2018 | Ingale | H04L 67/10 |
| 2020/0402622 | A1* | 12/2020 | Ishmael | G16H 10/60 |

OTHER PUBLICATIONS

MH-CURE Data Sheet. Available to the public on Jun. 6, 2017. Retrieved via Internet Archive from [http://www.mobileheartbeat.com/resources/] on [Aug. 12, 2020], 2 pages (Year: 2017).*

A Mobile Heartbeat Case Study, Yale-New Haven Hospital Using Smartphone Technology to Streamline Clinical Staff Communications, Mobile Heartbeat Clinical Communications, (2015).

A Mobile Heartbeat Case Study, Charlotte Hungerford Hospital, Using Smartphone Technology to Improve Patient Care, Mobile Heartbeat Clinical Communications, (2014).

Mobile Heartbeat Clinical Communications, "Key Considerations for Implementing Smartphone Technology in a Hospital Environment" (2014).

Mobile Heartbeat Clinical Communications, 2016 North American Secure Mobile Clinical Communication Entrepreneurial Company of the Year Award, 2016 Best Practices Awards (2016), Frost & Sullivan, 2016.

Mobilizing Healthcare for Improved Communication, Sprint Business for Companies with People in Them, Sprint Mobilizing Healthcare, E-Book.

A Mobile Heartbeat Case Study, Henry Mayo Newhall Hospital, Using Smartphone Technology to Improve Clinical Team Workflow, Mobile Heartbeat Clinical Communications (2014).

* cited by examiner

BI-DIRECTIONAL APPLICATION SWITCHING WITH CONTEXTUAL AWARENESS

CROSS REFERENCE TO RELATED APPLICATIONS

This application claims the benefit of and priority to U.S. Provisional Application No. 62/775,715, filed Dec. 5, 2018, which is hereby incorporated by reference in its entirety for all purposes.

BACKGROUND OF THE INVENTION

User devices such as smartphones and tablets have become ubiquitous in recent years. With this, the number of applications for these devices continues to increase year over year. Correspondingly, the number of applications with which users interact on a daily basis is higher now than it ever has been. Because applications are developed by different entities, users may be required to log into each independently and, even in cases where one set of credentials may be shared with more than one application, the functions of the applications may be so varied that time and information is likely to be lost as users navigate between and within different applications.

BRIEF DESCRIPTION OF THE DRAWINGS

The foregoing aspects and other features of the disclosed embodiments are explained in the following description, taken in connection with the accompanying drawings, wherein.

DETAILED DESCRIPTION OF THE INVENTION

Figure 1:
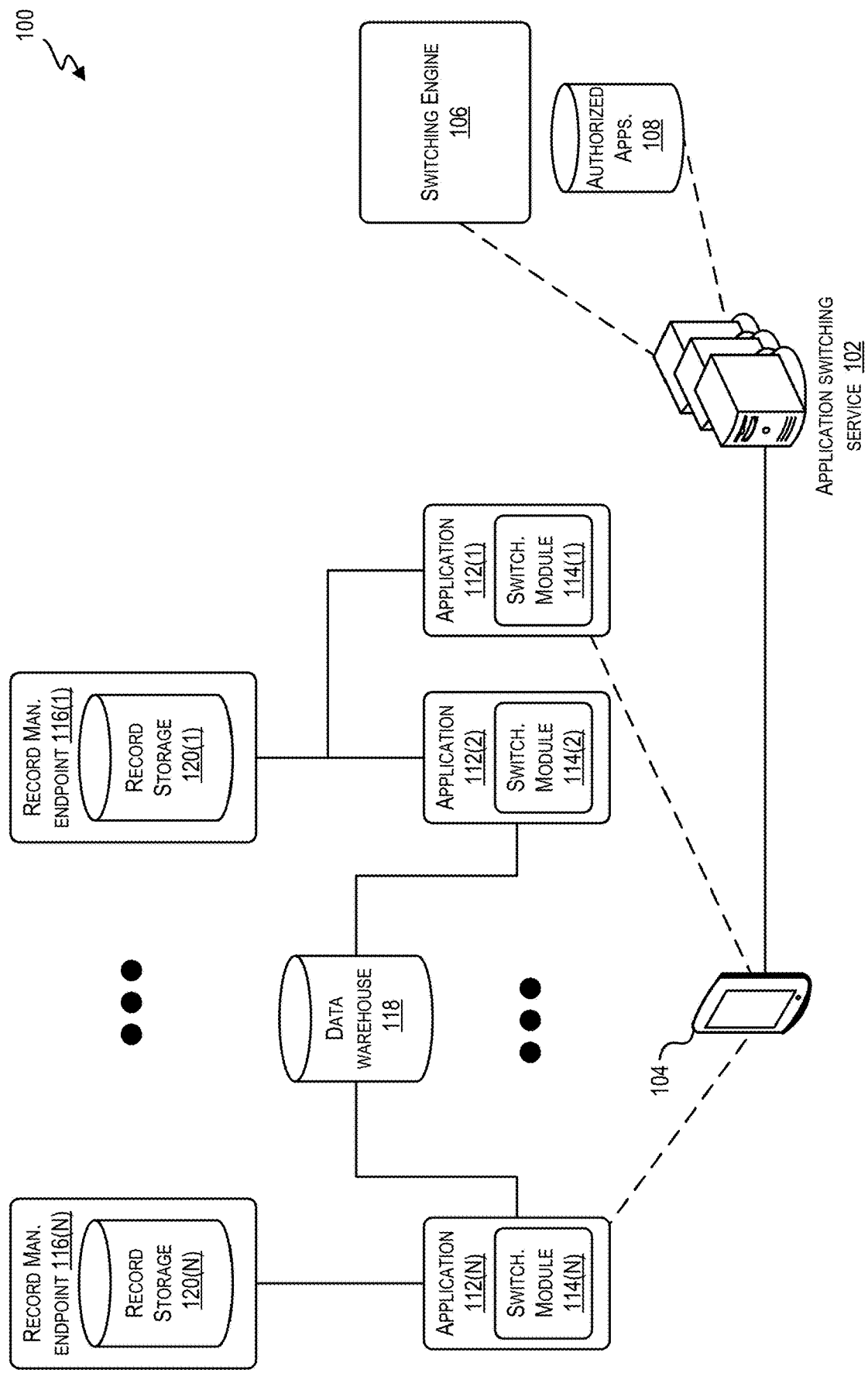
FIG. 1 is a schematic representation illustrating a system or architecture for implementing techniques relating to bi-directional application switching while maintaining contextual information.

In the following description, various examples will be described. For purposes of explanation, specific configurations and details are set forth in order to provide a thorough understanding of the examples. However, it will also be apparent to one skilled in the art that the examples may be practiced without the specific details. Furthermore, well-known features may be omitted or simplified in order not to obscure the example being described.

Examples described herein are directed to, among other things, techniques, systems, services, and devices for switching between two or more applications (e.g., applications on mobile devices) in a manner that maintains contextual awareness. For example, assume that an authorized user (e.g., medical provider or other authorized user) is viewing, in a first application (e.g., any suitable medical application such as a care team management application) on her mobile device, a summary record of a dependent user (e.g., a patient or other dependent user) for whom the authorized user is responsible. Using the techniques described herein, within the first application, the authorized user can select an option to switch to a second application (e.g., a different suitable medical application such as an electronic record application, lab results viewing application, live signal viewing application, and any other suitable application relating to viewing and/or interacting with a dependent user record or administering care to the dependent user). For example, the authorized user can select an icon that represents the second application. This action of selecting the icon will cause the second application to open on the mobile device, cause the authorized user to be logged in to the second application, and launch a particular view in the second application that is generated based on the context in which the authorized user was viewing the first application. For example, as the authorized user was viewing a summary record of the dependent user in the first application, the particular view in the second application—which depends on the function of the second application—may include a detailed dependent user record of the same dependent user. In this manner, the context of the first experience with the first application (e.g., login details for the authorized user, details about the dependent user whom the authorized user is seeing, and any other contextual information) can be captured and used to provide the second experience with the second application. This allows the authorized user to seamlessly switch between applications which include information about the dependent user without having to stop and log in, search for the dependent user information, or perform any other time-wasting exercise. This provides an improved and more efficient user experience for the authorized user by requiring fewer clicks, page throughs, selections, text inputs, and the like to achieve switch between applications presenting information about the same dependent user. This improved efficiency is possible by using the contextual identifier to share the context from the first application to the second application.

To enable the techniques described herein, an application switching service is provided that provides data to the mobile devices to enable the switching. In some examples, data is accessed from the application switching service application using one or more pre-defined routines (e.g., a set of application programming interface (API) calls). For example, the user device may request a contextual identifier that, when loaded by the user device, causes the actual switching to occur. The contextual identifier is generated by the application switching service and is based on contextual information associated with the session occurring with an initial application (e.g., which user is logged in, what dependent user record is relevant, and other similar contextual information). The contextual information is either provided in the request from the user device or determined by the application switching service. The contextual identifier can take the form of an encrypted list of parameter values (e.g., contextual information) that, when resolved by the user device, causes the user device to do the switching.

In one example, an application switching service is provided that is accessible using an API. The API enables an initial application to provide contextual switching with a target trusted application. The API specification defines conditions for authentication and encryption. A single key encryption protocol is used to encrypt dependent user data and other parameters passed between the applications. A unique application ID is maintained in a list of approved and trusted applications, i.e., those with which switching is supported. The context surrounding a dependent user, credentials for a hospital or other facility in which a provider is practicing, credentials for the target application, and any other contextual information are passed to the application switching service (e.g., from the mobile device). The service uses this information to generate a contextual identifier (e.g., an encrypted uniform resource locator (URL) and/or any other such data structure) that is passed back to the mobile device. Loading of the URL by the mobile device launches the target application with the appropriate context (e.g., logs in the authorized user, navigates to the dependent user record or other dependent user data, etc.).

In another example, a single sign-on technique is described that enables encrypted transfer of login credentials between applications on a mobile device. Using this technique, encrypted copies of usernames and passwords are passed between applications, instead of using tokens obtained from a remote server to provide credentials for one application to access other applications. For example, logging in to a first application can cause automatic logging in to other applications, with everything occurring on the mobile device (e.g., no passing of tokens to a server). The username is stored in an encrypted format on the mobile device, and the password is passed to the other applications when the first login is detected. This is achievable at least when the authorized user can use the same credentials for accessing both applications.

In yet another example, a technique for application switching is described that selectively determines a target application from a set of applications on a mobile device based on a notification received while an initial application is open on the mobile device. For example, an alarm, alert, or other notification registered in the initial application is used as a trigger to jump to the target application. For example, a dependent user alarm registered in the initial application triggers a notification for the user to view the waveform data that caused the alarm in the target application. From the notification, the user can select to view the waveform data in the target application. The switching to the target application maintains contextual awareness about the dependent user, as described elsewhere herein. In some examples, the alarm may be received from a telemetry system or from another system outside of the dependent user record. In this example, responsive to receiving the alarm, the application can place a button for launching a different application for responding to the alarm and/or viewing information relating to the alarm (e.g., a application for reviewing real-time waveform data).

In yet another example, a technique for application switching is described that is dependent on detecting a dependent user context from an initial application. A set of contextual rules define what action occurs given a set of dependent user conditions (e.g., the dependent user context). For example, if a dependent user is not admitted to a hospital, selection of an icon to switch to a target application may take the user to a first screen in the target application. Once the dependent user has been admitted, selection of the same icon make take the user to a completely different screen in the target application, even though the primary context in the initial application remained the same (e.g., the authorized user is viewing some record associated with the dependent user). The authorized user may not even know that the admission status of the dependent user has been updated, but the system can adapt by adjusting which portion of the target application is most appropriate given the change to the dependent user's record (e.g., the admission status change). Thus, the context of the dependent user can change the function of the switching.

In yet another example, a technique for application switching is described that maintains context in both directions (e.g., from an initial application to a target application and back from the target application to the initial application). For instance, a first switch from the initial application to the target application may involve dependent user X or portion Y of dependent user X's record. While in the target application, the authorized user can navigate away from dependent user X's record in favor of viewing a record of dependent user A or a portion B of dependent user A's record. A second switch from the target application back to the initial application maintains the most recent context, as registered by the target application (e.g., the authorized user interacting with information about dependent user A or a portion B of dependent user A's record).

Turning now to figures, FIG. 1 illustrates a system 100 or architecture for implementing techniques relating to bi-directional application switching while maintaining contextual information, according to at least one example. The system 100 includes an application switching service 102 and a user device 104. The application switching service 102 can include any suitable combination of hardware and/or software configured to implement the techniques described herein. In some examples, the application switching service 102 may be implemented by one or more virtual servers and/or a combination of local and virtual servers. To this end, the application switching service is implemented by one or more service provider computers or other server computers that include any suitable combination of processors, memory devices, input/output devices, interfaces (e.g., API, web interface, user interface, etc.), operating systems, and the like.

The user device 104 is any suitable user device including, for example, a mobile phone, wearable device, laptop, desktop computer, cable box, streaming device, and any other device suitable for communicating with the application switching service 102 in a client-server relationship. Thus, the user device 104 includes any suitable combination of processors, memory devices, input/output devices, interfaces, operating systems, and the like.

The application switching service 102 and the user device 104 may be in network communication via one or more networks including, for example, a cellular network, the Internet, a cable network, local area network, wide area network, wireless network, and any other suitable network.

The application switching service 102 includes a switching engine 106 and an authorized application database 108. The switching engine 106 is configured to implement the techniques described with reference to the application switching service 102. For example, the switching engine 106, among other things, generates contextual identifiers, provides for communication with the user device 104, and accesses dependent user records, in some circumstances.

The authorized application database 108 is configured to store information that identifies which applications are authorized or otherwise approved to use the application switching service 102. The information may be stored in the form of unique application identifiers that identify the applications. The process for approving an application can include confirming the trustworthiness of the application using one or more automated and/or manual efforts. For example, security standards relating to safeguarding information can be established and the applications can be compared to these security standards to ensure they comply. In some examples, the standards may require support for one or more encryption techniques such as, for example, symmetrical private key encryption. Once an application has been approved, the application can be provided a private key and the application's unique application identifier can be added to the authorized application database 108. In some examples, when an application switching request is received by the application switching service 102 to switch to a target application, the application switching service 102 can confirm that the target application is approved by accessing the authorized application database 108.

Within memory of the user device 104 can be stored one or more computer applications 112(1)-112(N). In some examples, the computer applications 112 are accessed via a network and may be considered web applications. In accordance with the techniques described herein, the computer applications 112 also include switching modules 114(1)-114(N). The switching modules 114 are any suitable combination of software and/or hardware modules configured to perform the techniques described herein. In some examples, the switching modules 114 may maintain information regarding how to communicate with the switching engine 106. In some examples, the switching modules 114 may be used to associate application identifiers and sets of contextual parameters with switching selectors (e.g., an icon that represents a target application to which application switching is requested).

The ellipsis as shown separating the applications 112(N) and 112(2) represent that any other suitable number of applications are contemplated. Other uses of ellipsis throughout this document have a similar meaning.

The applications 112 can be associated with one or more record management endpoints 116(1)-116(N) and/or a clinical data warehouse 118. The record management endpoints 116 are electronic record (EMR) platforms configured to manage dependent user records, manage provider practices, and perform other functions with respect to storing dependent user data. To this end, each of the record management endpoints 116 includes a record storage 120 to store electronic dependent user records. In some examples, each of the applications 112 is configured to access a single record management endpoint 116 and the clinical data warehouse 118. In other examples, multiple applications 112 may be supported by a single record management endpoint 116 (e.g., the applications 112(1) and 112(2)).

The clinical data warehouse 118 (and any other data store discussed herein) may include one or more data stores, which may be distributed throughout two or more different locations (e.g., present on different devices, which can include devices of different entities and/or a cloud server). In some examples, the clinical data warehouse 118 includes a general data store, an operational data store, and an entity-based data store. Within each of these data stores is stored data. Depending on the structure of the particular data store, certain data stores may include rules for reading and writing. The clinical data warehouse 118 includes records, tables, arrays, and the like, which may be relational or non-relational. Depending on the data store, records for individual entities, business and analytics information, output data from one or more application, and the like may be retained. The data within the clinical data warehouse 118 include elements or tags such that a particular data (e.g., for a single entity, protocol, etc.) can be retrieved.

Figure 2:
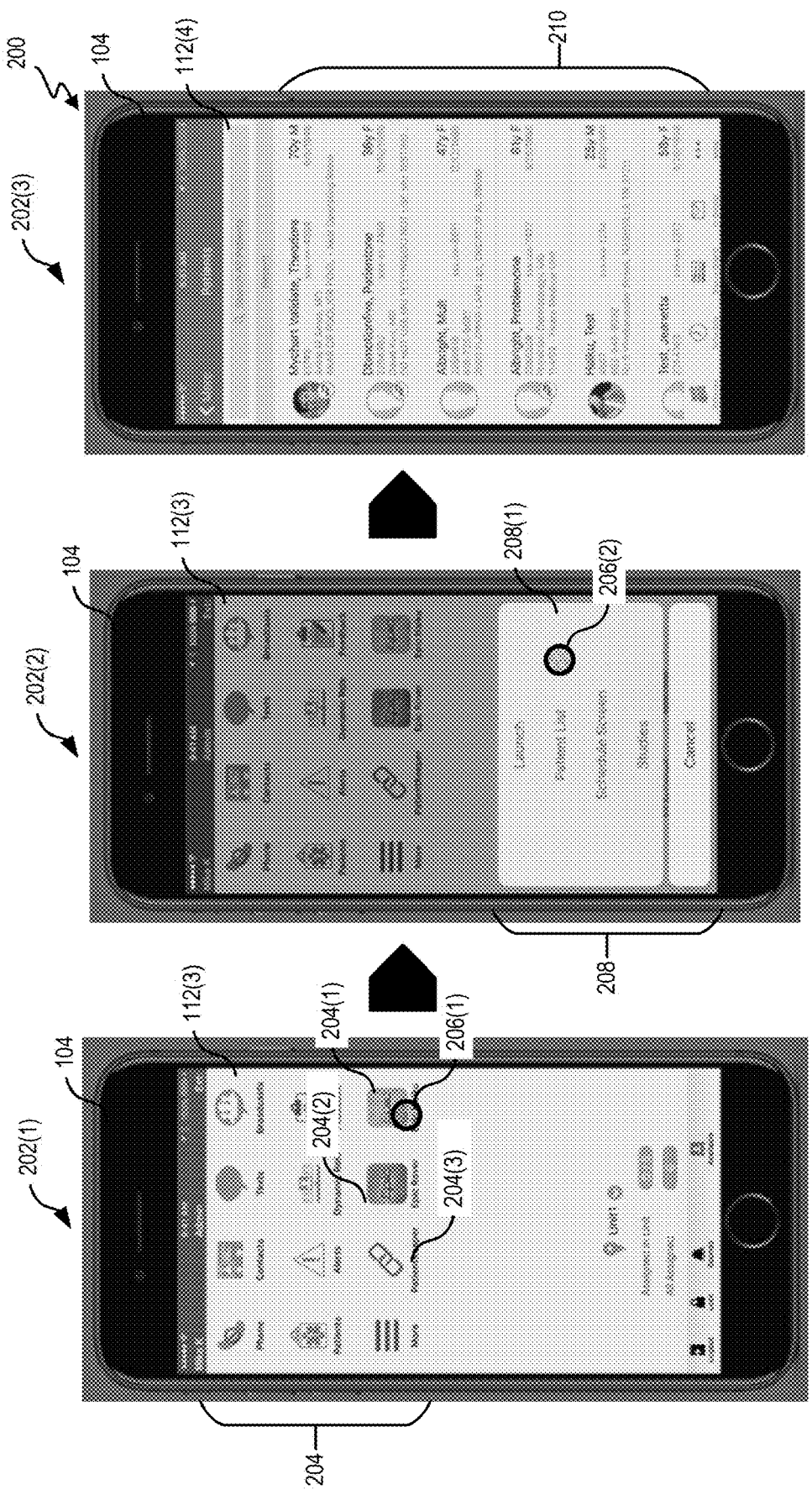
FIG. 2 is a schematic representation illustrating a system diagram for contextual switching from an initial application to a target application.

FIG. 2 illustrates a system diagram 200 for contextual switching from an initial application to a target application, according to at least one example. The diagram 200 includes the user device 104 in various states 202(1)-202(3).

At the state 202(1), the user device 104 is shown presenting an initial application 112(3). The initial application 112(3) includes various user interface elements 204 which represent different functionalities accessible from within the initial application 112(3). Selection of any one of the user interface elements 204 will cause the user device 104 to perform the associated function such as, for example, place a phone call, access contacts, send a message, broadcast a message, identify dependent users, review alerts, provide feedback, and the like. In some examples, particular ones of the user interface elements 204 may be referred to as switching selector user interface elements which, when selected, cause application switching to a respective target application. For example, the user interface elements 204(1)-204(3) are examples of switching selectors. The switching module(s) associated with the initial application 112(3) may define using metadata or other suitable data information for each of switching selector user interface elements 204(1)-204(3). For example, such metadata may include an application identifier corresponding to the target application, a list of parameters relevant to the switching (e.g., dependent user identifier, user identifier, credentials, and the like).

As illustrated in FIG. 2, a user input 206(1) is shown as having selected the user interface element 204(1) corresponding to a target application 112(4). In response, the view at state 202(2) may be presented. In the state 202(2), a set of options 208 is presented within the initial application 112(3). The set of options 208 correspond to the target application 112(4), and represent different locations within the target application 112(4) to which can be navigated as part of the switching. As illustrated, a user input 206(2) is shown as having selected the option 208(1) corresponding to a dependent user list 210.

The user input 206(2) may cause the user device 104 to communicate with the server computer such as the application switching service 102 to obtain information (e.g., a contextual identifier) in order to switch to the target application 112(4) and navigate to the dependent user list 210 in the target application 112(4) without additional user input. In particular, the user is not required to log in to the target application 112(4), search for the dependent user list 210, or perform any other actions at the target application 112(4). In this manner, the context of the earlier interactions at the initial application 112(3) is maintained. The dependent user list 210 may be associated with the authorized user that is logged in to the initial application 112(3).

Figure 3:
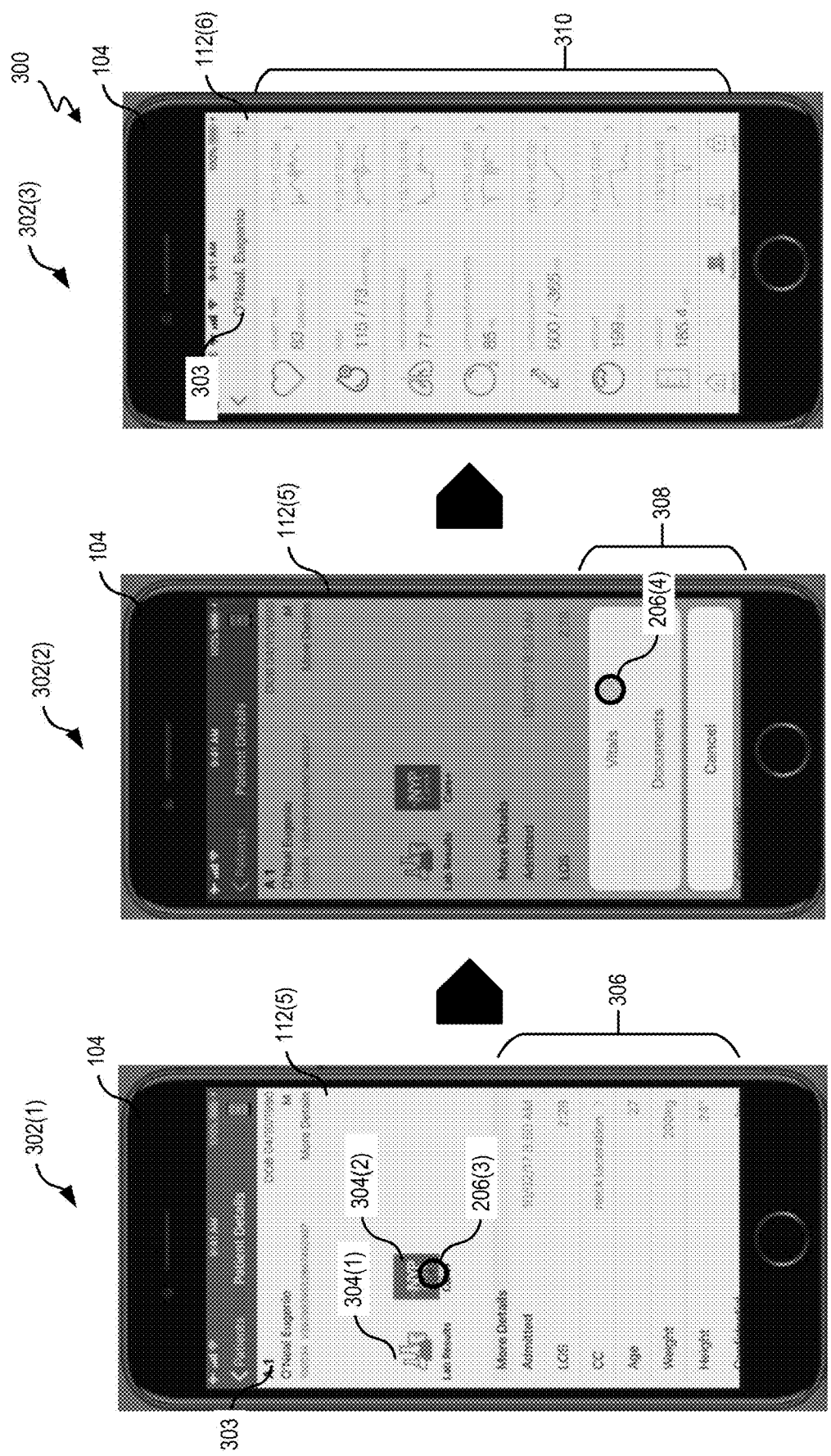
FIG. 3 is another schematic representation illustrating a system diagram for contextual switching from an initial application to a target application.

FIG. 3 illustrates a system diagram 300 for contextual switching from an initial application to a target application, according to at least one example. The diagram 300 includes the user device 104 in various states 302(1)-302(3).

At the state 302(1), the user device 104 is shown presenting an initial application 112(5). The initial application 112(5) includes various user interface elements 304 which represent different functionalities accessible from within the initial application 112(5). Selection of any one of the user interface elements 304 will cause the user device 104 to perform the associated functions. In this example, user interface elements 304(1) and 304(2) function as switching selectors that, when selected by a user input, cause switching to the target applications depicted by the user interface elements 304(1) and 304(2).

The initial application 112(5) presents dependent user information 306 (e.g., admitted date, LOS, CC, age, weight, height, etc.) that is particular to a dependent user 303 (e.g., "O'Neal Eugenio"). The initial application 112(5) may include a first amount of information about the dependent user 303. However, in order to access additional information about the dependent user 303, the authorized user may need to access a different application, represented by user interface elements 304(1) and 304(2).

In FIG. 3, a user input 206(3) is shown selecting the user interface element 304(2). The user input 206(3) triggers a process for loading a target application 112(6) that corresponds to the user interface element 304(1).

In some examples, selection of the user interface element 304(2) may cause presentation of a set of options 308 at the user device 104. The set of options 308 correspond to the target application 112(6), and represent different locations within the target application 112(6) to which can be navigated as part of the switching. As illustrated, a user input 206(4) is shown as having selected the option 308(1) corresponding to vitals.

In some examples, the set of options 308 is not presented and/or the selection of one of the set of options 308 is programmatic based on user preferences. In any event, the user input 206(4) may cause the user device 104 to communicate with the server computer such as the application switching service 102 to obtain information (e.g., a contextual identifier) in order to switch to the target application 112(6) and navigate to the vitals 310 in the target application 112(6) without additional user input. In particular, the user is not required to log in to the target application 112(6), search for the dependent user 303, search for the vitals 310 of the dependent user 303, or perform any other actions at the target application 112(6). In this manner, the context of the earlier interactions at the initial application 112(4) is maintained. The authorized user can return to the initial application 112(4) by selecting a back button in the user interface.

Figure 4:
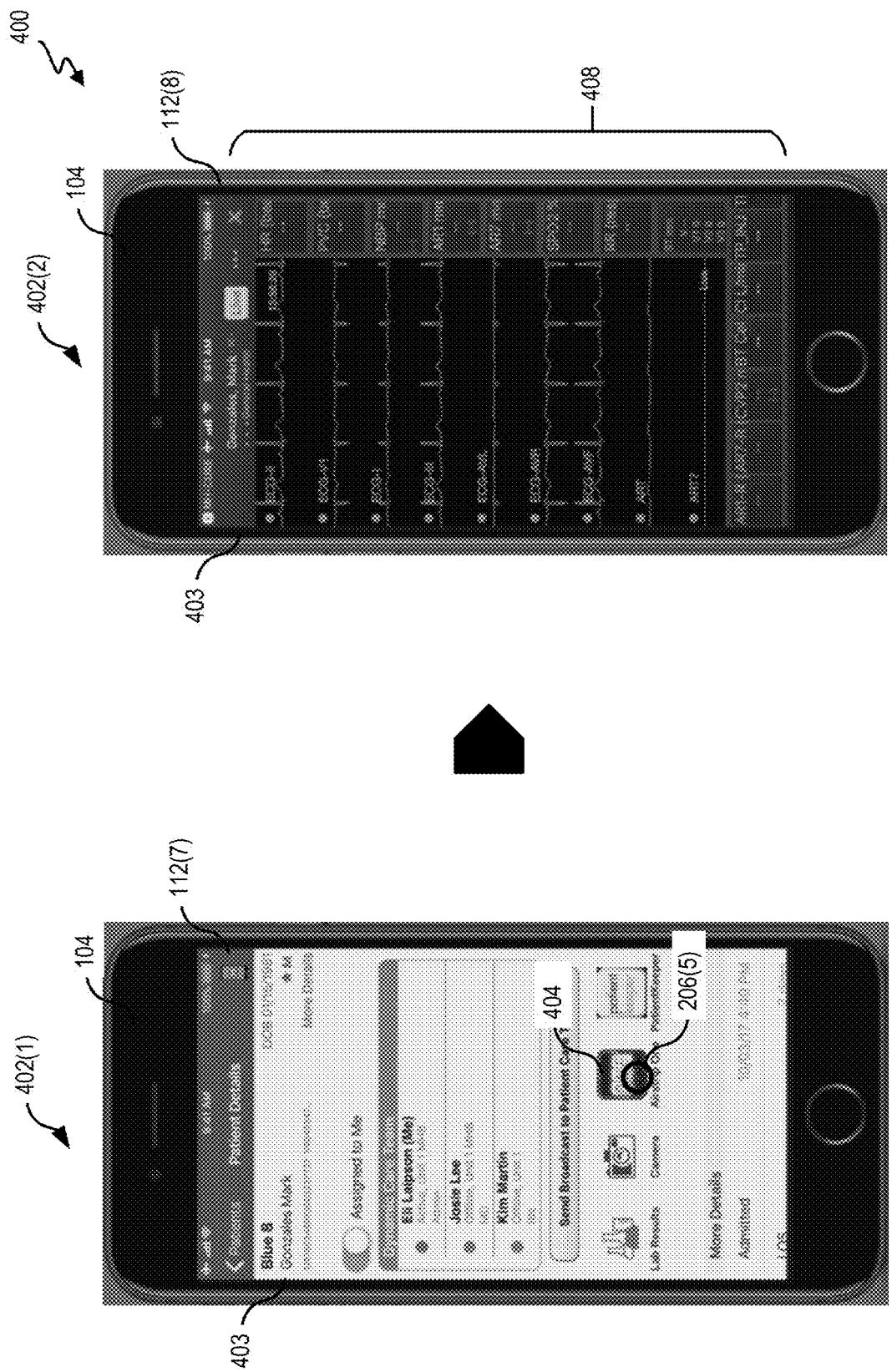
FIG. 4 is another schematic representation illustrating a system diagram for contextual switching from an initial application to a target application.

FIG. 4 illustrates a system diagram 400 for contextual switching from an initial application to a target application, according to at least one example. The diagram 400 includes the user device 104 in various states 402(1) and 402(2).

At the state 402(1), the user device 104 is shown presenting an initial application 112(7). The initial application 112(7) includes various user interface elements 404 which represent different functionalities accessible from within the initial application 112(7). Selection of any one of the user interface elements 404 will cause the user device 104 to perform the associated functions. In this example, user interface element 404 functions as a switching selector that, when selected by a user input 206(05), causes switching to the target application depicted by the user interface element 404. In this example, the initial application 112(7) identifies a dependent user 403 (e.g., "Gonzales Mark"). After the switching has occurred, the target application 112(8) also identifies the dependent user 403. The target application 112(8) also identifies live waveform data 408 of the dependent user 403.

Figure 5:
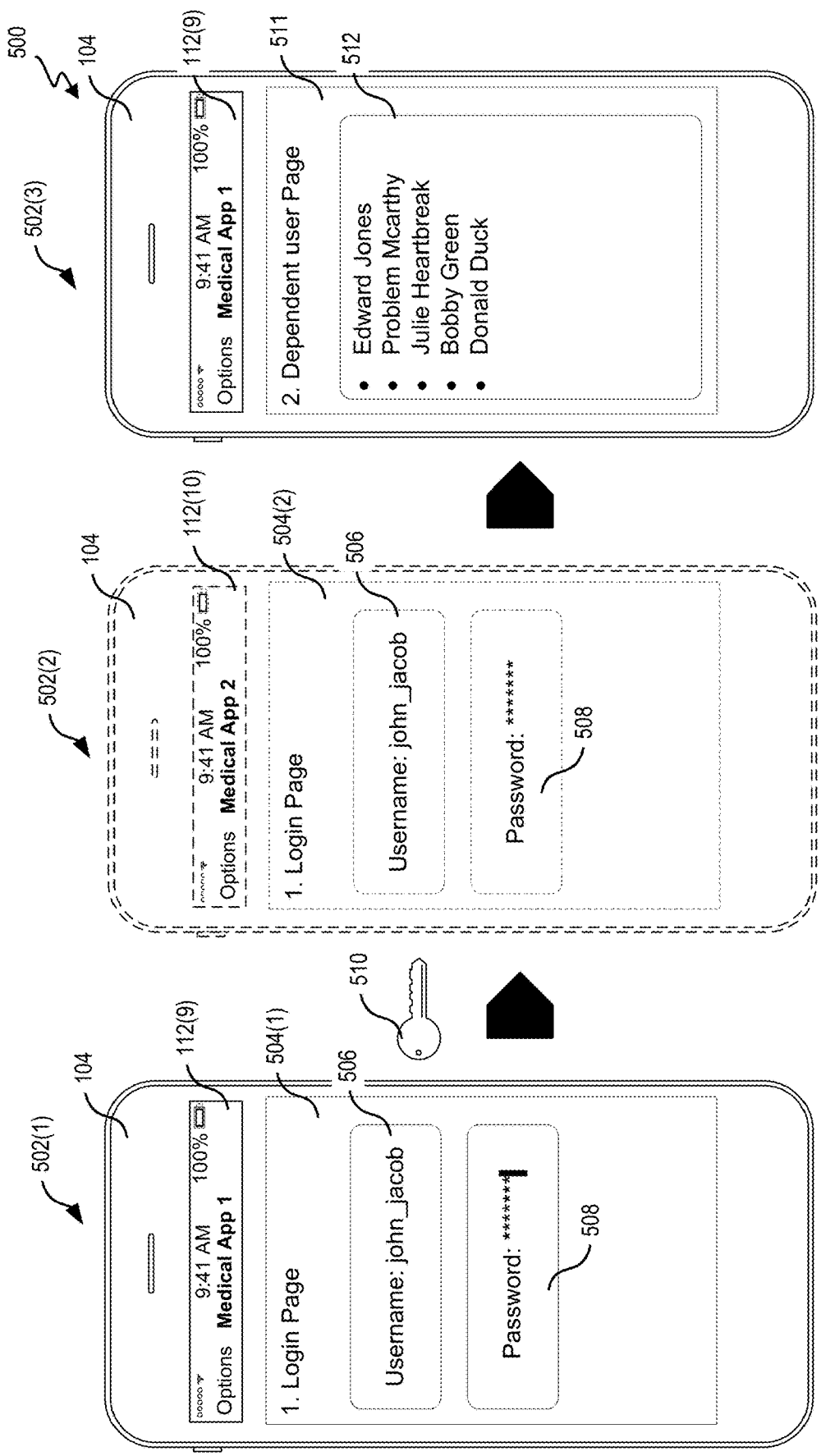
FIG. 5 is a schematic representation illustrating a system diagram for automatic logging in to a second application based on a detected login at a first application.

FIG. 5 illustrates a system diagram 500 for automatic logging in to a second application based on a detected login at a first application, according to at least one example. The diagram 500 includes the user device 104 in various states 502(1)-502(3).

At the state 502(1), a login screen 504(1) of a first application 112(9) is presented. A user, such as a provider, has entered his username 506 and password 508 at the login screen 504(1). As the user completes the password 508 and submits the credentials for verification, an automated process will begin that logs the user in to other applications such as the second application 112(10) programmatically and without contacting a remote server for a token. In this manner, the process illustrated by FIG. 5 provides for a simplified single sign-on process that stores an copy of the username 506 on the user device 104 and passes an encrypted version of the password 508 to other applications.

In particular, the user can be logged in to the second application 112(10) in the background, i.e., with little to no disruption to the current experience with the first application 112(9). In some examples, a login screen 504(2) of the second application 112(10) is shown transitorily while the username 506 and the password 508 are authenticated. Thus, the state 502(2) is depicted in dashed lines.

The first application 112(9) uses a private key 510 to encrypt the password 508 and, in some examples, the username 506 prior to passing these credentials to the second application 112(10). The second application 112(10) uses the same private key 510 to decrypt the credentials.

After the user has been logged in to the second application 112(10), the first application 112(9) is presented again, as represented by the state 502(3). In the state 503(3), a dependent user page 511 is presented along with a list of dependent users 512. The list of dependent users 512 can be specific to the user, i.e., provider "john_jacob."

As discussed, in some examples, the state 502(2) is actually never presented to the user, but instead occurs as a background process. In some examples, other applications 112 can be logged in to in addition to the second application 112(10). For example, the first application 112(9) can function as a master application and access a database of application identifiers for a set of trusted applications. Once a login is detected at the first application 112(9), the user can be logged in to all other trusted applications.

Figure 6:
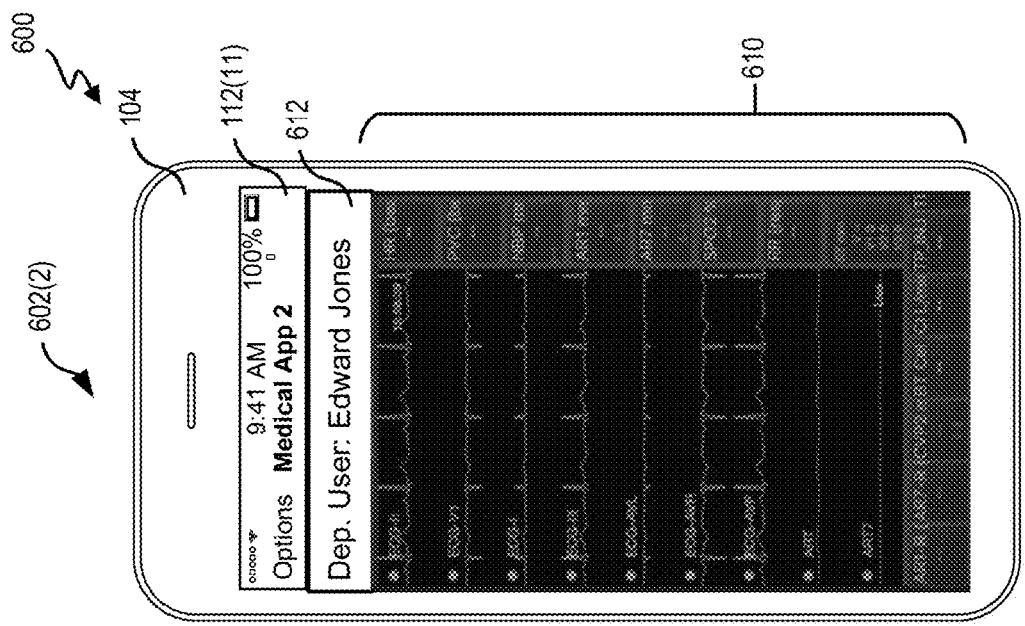
FIG. 6 is a schematic representation illustrating a system diagram for selectively switching to a target application based on a notification received at a first application.
Figure 6:
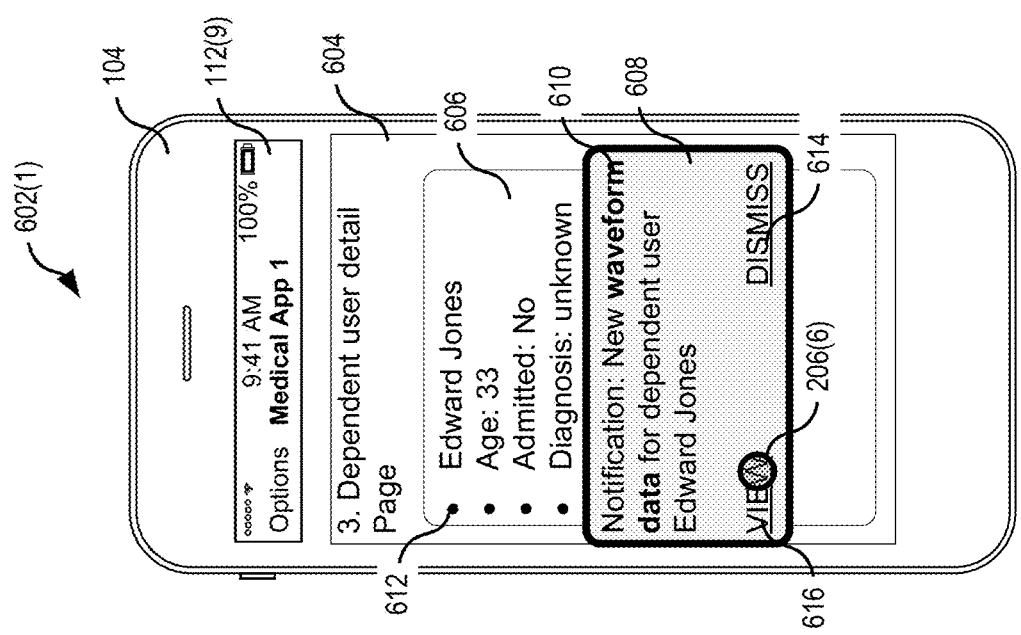

FIG. 6 illustrates a system diagram 600 for selectively switching to a target application based on a notification received at a first application, according to at least one example. The diagram 600 includes the user device 104 in various states 602(1) and 602(2).

At the state 602(1), dependent user detail page 604 of a first application 112(9) is presented. The dependent user detail page 604 includes dependent user details 606 for a dependent user 612, (e.g., "Edward Jones"). In the state 602(1), a notification 608 is also presented. In some examples, the notification 608 may be generated and presented in the first application 112(9) when the waveform data 610 is available. For example, a listener in the first application 112(9) or in the application switching service 102 can monitor a dependent user record, lab results, and any other messages that identify the dependent user 612. Rules define the conditions under which an update to the record or other data may trigger a notification to switch applications. In this example, once the waveform data 610 becomes available, the user interface of the first application 112(9) may be updated to include the notification 608.

The notification 608 includes at least two options, dismiss 614 and view 616. Selection of the dismiss option 614 will dismiss the notification 608 and not switch from the first application. Selection of the view option 616, as illustrated by user input 206(6), causes switching to a second application 112(11), as shown in the state 602(2). Not only is the second application 112(11) presented, but the context from the first application 112(9), i.e., viewing of the record of the dependent user 612, is maintained and presented in the second application 112(11). In this example, the waveform data 610 for the dependent user 612 is presented by the second application 112(11).

Figure 7:
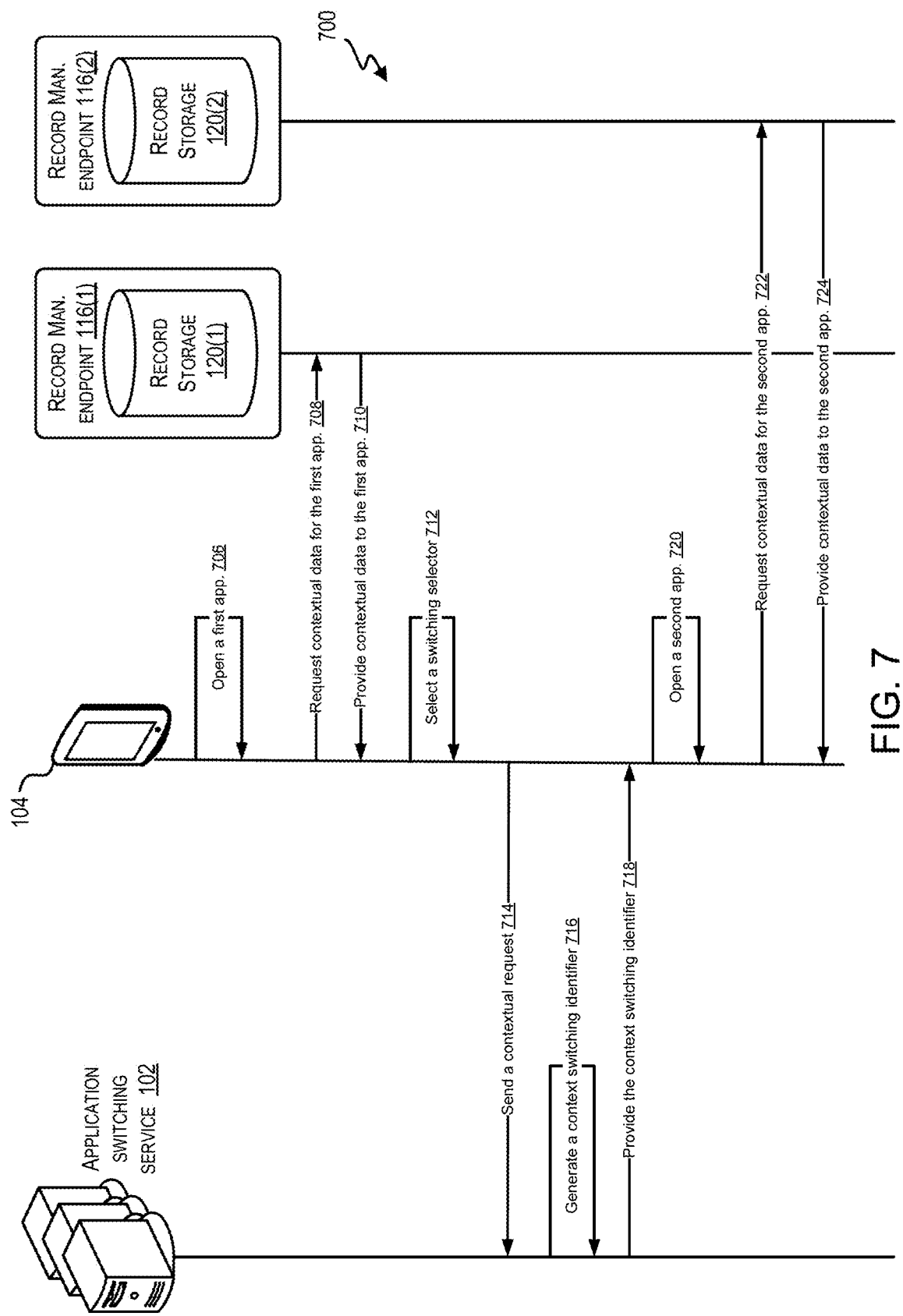
FIG. 7 is a schematic representation illustrating a process for switching from a first application to a second application while maintaining contextual information.
Figure 8:
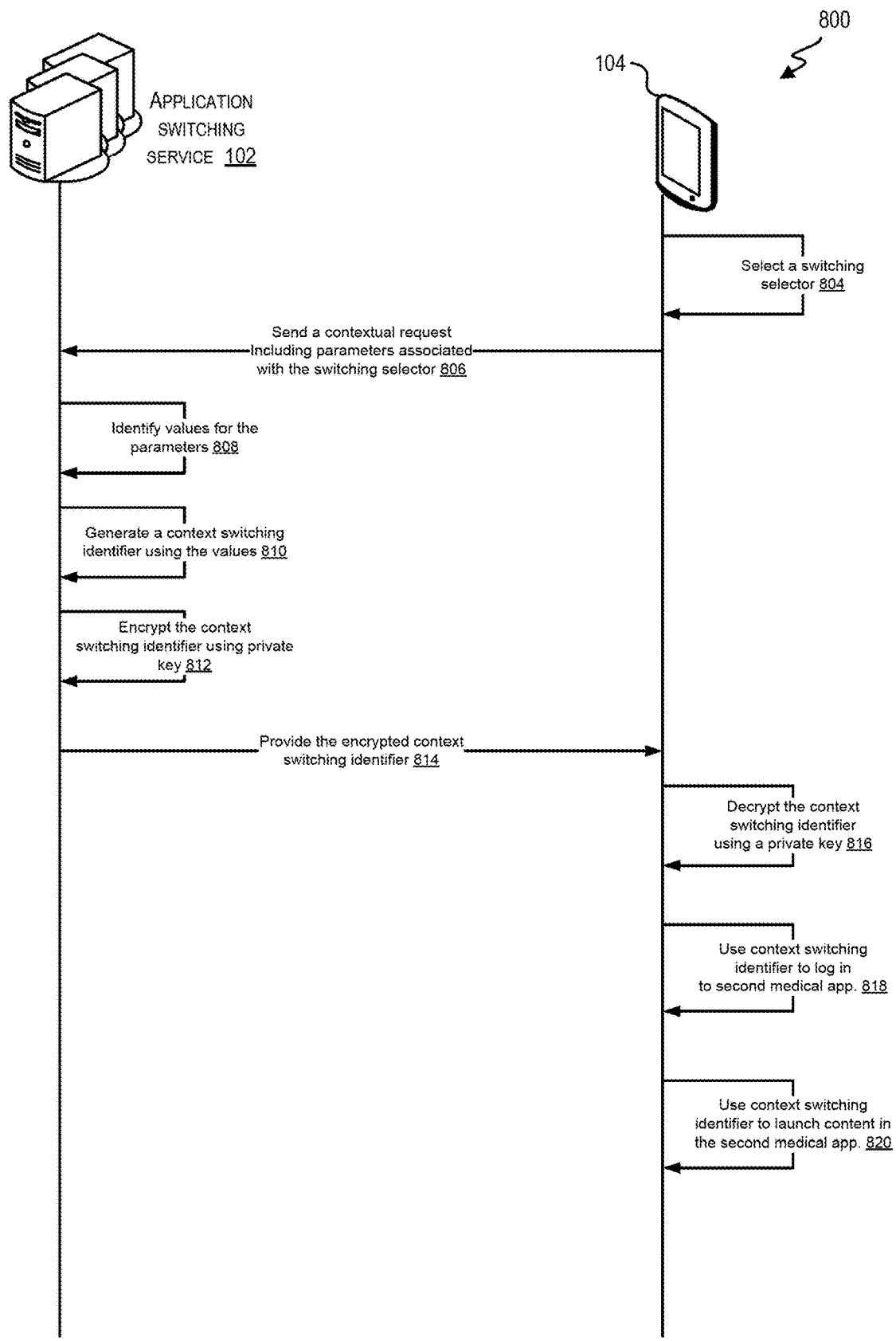
FIG. 8 is another schematic representation illustrating a process for switching from a first application to a second application while maintaining contextual information.

FIGS. 7 and 8 illustrate example swim diagrams showing respective processes 700 and 800 as described herein. These processes depict example operations which may be performed by the various components from the system 100.

FIG. 7 illustrates an example process 700 for switching from a first application to a second application while maintaining contextual information, as described herein. The swim diagram includes the application switching service 102, the user device 104, and the record management endpoints 116(1) and 116(2).

The process 700 begins at 706 by opening a first application. This is performed by the user device 104. In some examples, the first application will be opened responsive to user input. In other examples, the first application will be opened upon the user device 104 being unlocked or assigned to the user (e.g., as part of a fungible set of user devices that are checked out by users for daily use). In some examples, the user may also log in to the first application using user credentials. In other examples, the user may be automatically logged in to the first application upon opening the first application or without opening the first application.

At 708, the process 700 includes requesting contextual data for the first application. This is performed by the user device 104. The contextual data can relate to a dependent user and/or the user who is logged in to the user device 104. The first application can request the contextual data from the record management endpoint 116(1). For example, the first application may be associated with and/or otherwise rely on data from the record management endpoint 116(1) to populate the first application.

At 710, the process 700 includes providing the contextual data to the first application. This is performed by the record management endpoint 116(1). The contextual data may be stored in the record storage 120(1). In some examples, the request provided at 708 may include parameters and the contextual data may be provided as the values that match the parameters. The first application uses the contextual data to populate aspects of the first application. For example, the first application can identify a dependent user and can identify a user logged in to the application.

At 712, the process 700 includes selecting a switching selector. This is performed by the user device 104, e.g., as a user selects the switching selector. The switching selector is a user interface element that has been previously associated with data for application switching. In some examples, the switching selector identifies the application to which the first application will be switched. The switching selector can be presented dynamically based on fulfillment of some conditions and/or may be static. A set of parameters can be associated with the switching selector. These parameters identify the type of data that can be switched from the first application to a second application. Parameters can be written in metadata or in any other manner.

At 714, the process 700 includes sending a contextual request. This is performed by the user device 104. The user device 104 can send the contextual request responsive to selection of the switching selector at 712. The contextual request can include values corresponding to the parameters associated with the switching selector.

At 716, the process 700 includes generating a context switching identifier. This is performed by the application switching service 102. The context switching identifier can include a uniform resource locator (URL) that includes an encrypted list of values corresponding to the parameters associated with the switching selector and an application identifier of the second application to which the switching selector switches.

At 718, the process 700 includes providing the contextual identifier. This can be performed by the application switching service 102 to the user device 104. When the user device 104 resolves the context switching identifier, the user device 104 is configured to decrypt the encrypted list of values to identify the contextual data from the context switching identifier.

At 720, the process 700 includes opening a second application. This is performed by the user device 104. In some examples, opening the second application is responsive to receiving the context switching identifier. For example, the context switching identifier may cause the user device 104 to open the second application.

At 722, the process 700 includes requesting contextual data for the second application. This is performed by the user device 104. The user device 104 can request the contextual data from the record management endpoint 116(2) based on the context switching identifier.

At 724, the process 700 includes providing contextual data to the second application. This is performed by the record management endpoint 116(2). The record management endpoint 116(2) provides the contextual data to the user device 104 for loading in the second application.

FIG. 8 illustrates an example process 800 for switching from a first application to a second application while maintaining contextual information, as described herein. The swim diagram includes the application switching service 102 and the user device 104.

The process 800 begins at 804 by selecting a switching selector. This is performed by the user device 104. The switching selector can be presented in a first application.

At 806, the process 800 includes sending a contextual request including parameters associated with the switching selector. This is performed by the user device 104. The contextual request is sent to the application switching service 102. The contextual request, in some examples, may also include the values corresponding to the parameters. For example, the user device 104 may gather the values, encrypt the values, and send them to the application switching service 102.

At 808, the process 800 includes identifying values for the parameters. This is performed by the application switching service 102. For example, the contextual request can be an API call and, responsive to receiving the contextual request, the application switching service 102 may perform the subsequent operations described herein.

At 810, the process 800 includes generating a context switching identifier using the values. This is performed by the application switching service 102. The context switching identifier can include a parameterized list of the values, which can take the form of a URL. In some examples, the URL includes a token to access the values. Thus, the values can be included in the context switching identifier or accessible at a location identified by the context switching identifier.

At 812, the process 800 includes encrypting the context switching identifier using a private key. This is performed by the application switching service 102. The private key can be shared with the other applications in order to decrypt the context switching application.

At 814, the process 800 includes providing the encrypted context switching identifier. This is performed by the application switching service 102 and provided to the user device 104.

At 816, the process 800 includes decrypting the context switching identifier using a private key. This is performed by the user device 104, and may be responsive to receiving the context switching identifier. In particular, the user device 104 can use the symmetrical key to the used to encrypt the context switching identifier to decrypt the package.

At 818, the process 800 includes using the context switching identifier to log in to a second application. This is performed by the user device 104. A first value of the context switching identifier can be used to log the user in to the second application. The first value can be user credentials.

At 820, the process 800 includes using the context switching identifier to launch content in the second application. This is performed by the user device 104. A second value of the context switching identifier can be used to launch the content in the second application. The content can correspond to the context originally presented in the first application.

FIGS. 9, 10, 11, 12, 13 and 14 illustrate example flow diagrams showing respective processes 900, 1000, 1100, 1200, 1300, and 1400 as described herein. These processes 900, 1000, 1100, 1200, 1300, and 1400 are illustrated as logical flow diagrams, each operation of which represents a sequence of operations that can be implemented in hardware, computer instructions, or a combination thereof. In the context of computer instructions, the operations represent computer-executable instructions stored on one or more computer-readable storage media that, when executed by one or more processors, perform the recited operations. Generally, computer-executable instructions include routines, programs, objects, components, data structures, and the like that perform particular functions or implement particular data types. The order in which the operations are described is not intended to be construed as a limitation, and any number of the described operations can be omitted or combined in any order and/or in parallel to implement the processes.

Additionally, some, any, or all of the processes may be performed under the control of one or more computer systems configured with executable instructions and may be implemented as code (e.g., executable instructions, one or more computer programs, or one or more applications) executing collectively on one or more processors, by hardware, or combinations thereof. As noted above, the code may be stored on a computer-readable storage medium, for example, in the form of a computer program comprising a plurality of instructions executable by one or more processors. The computer-readable storage medium is non-transitory.

Figure 9:
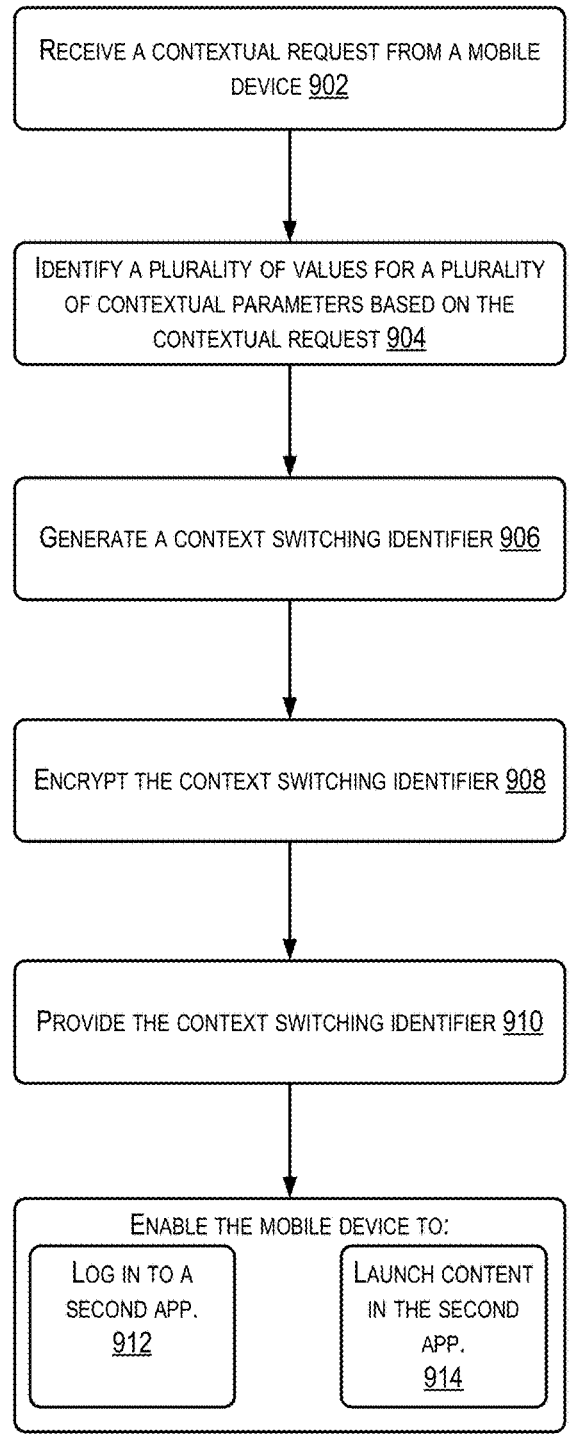
FIG. 9 is an exemplary flowchart illustrating the process including example acts or techniques relating to bi-directional application switching while maintaining contextual information.

FIG. 9 illustrates the process 900 including example acts or techniques relating to bi-directional application switching while maintaining contextual information, according to at least one example. The switching engine 106 within the application switching service 102 and/or the switching module 114 within an application 112 of the user device 104 performs the process 900 of FIG. 9.

The process 900 begins at 902 by receiving a contextual request from a mobile device. The contextual request is initiated by an authorized user selecting a switching selector within a first application of the mobile device. The contextual request also identifies a second application of the mobile device. For example, the switching selector can be presented within a page of the first application. The switching selector is also associated with the second application. For example, the switching selector can identify the second application by name.

At 904, the process 900 includes identifying a plurality of values for a plurality of contextual parameters based on the contextual request. The plurality of values define a context of the first application at a time when the contextual request was received. The plurality of contextual parameters define what types of contextual data can be passed between the first application and the second application. The plurality of values are parameter values, i.e., the data from the first application that correspond to the contextual parameters. The plurality of contextual parameters are associated with the switching selector.

At 906, the process 900 includes generating a context switching identifier. Generating the context switching identifier is based on the plurality of values and an application identifier associated with the second application.

At 908, the process 900 includes encrypting the context switching identifier. Encrypting the context switching identifier can be performed by using a private key.

At 910, the process 900 includes providing the context switching identifier. This can include providing the context switching identifier to the mobile device.

At 912, the process 900 includes enabling the mobile device to use the context switching identifier to log the user in to the second application. This can include using a first value of the plurality of values. For example, the first value can be a username and/or a password that is capable of logging in to the second application. The first value is collected at the first application.

At 914, the process 900 includes enabling the mobile device to use the context switching identifier to launch content in the second application using a second value of the plurality of values. The second value corresponds to a dependent user. For example, the first application was previously used to view and/or interact with a record of the dependent user. The second value can be a dependent user identifier that is capable of accessing dependent user data in the second application. The second value is collected at the first application.

Figure 10:
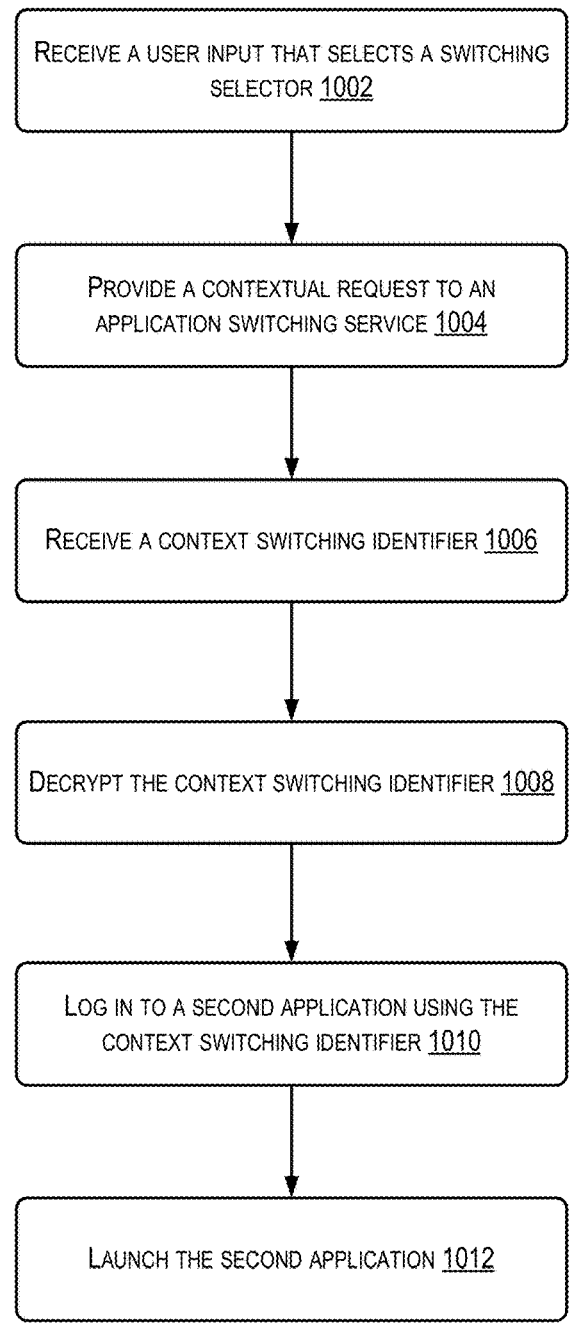
FIG. 10 is another exemplary flowchart illustrating the process including example acts or techniques relating to bi-directional application switching while maintaining contextual information.

FIG. 10 illustrates the process 1000 including example acts or techniques relating to bi-directional application switching while maintaining contextual information, according to at least one example. The switching engine 106 within the application switching service 102 and/or the switching module 114 within an application 112 of the user device 104 performs the process 1000 of FIG. 10.

The process 1000 begins at 1002 by receiving a user input that selects a switching selector. The switching selector is presented in a first application. The first application presents first information associated with a dependent user. The switching selector identifies a second application and is associated with a plurality of contextual parameters. For example, metadata can be used to identify the second application (e.g., by the application identifier) and the plurality of contextual parameters.

At 1004, the process 1000 includes providing a contextual request to an application switching service. Providing the contextual request can be performed responsive to receiving the user input. The contextual request can at least identify the plurality of parameters. For example, a mobile device can generate the contextual request in response to user selection of the switching selector.

At 1006, the process 1000 includes receiving a context switching identifier. The context switching identifier can include a plurality of values corresponding to the plurality of parameters. The context management service can generate the context switching identifier prior to providing it to the mobile device. The plurality of values identify the dependent user and user login credentials for an authorized user who is interacting with the first application.

At 1008, the process 1000 includes decrypting the context switching identifier. For example, because the context switching identifier was generated by the application switching service and encrypted using a private key, the mobile device can use a corresponding private key to decrypt the context switching identifier and identify the values stored by the context switching identifier.

At 1010, the process 1000 includes logging a user in to the second application using the user login credentials. The login credentials can be obtained as a value from the context switching identifier.

At 1012, the process 1000 includes launching the second application. Launching the second application can include launching the second application to display second information associated with the dependent user.

Figure 11:
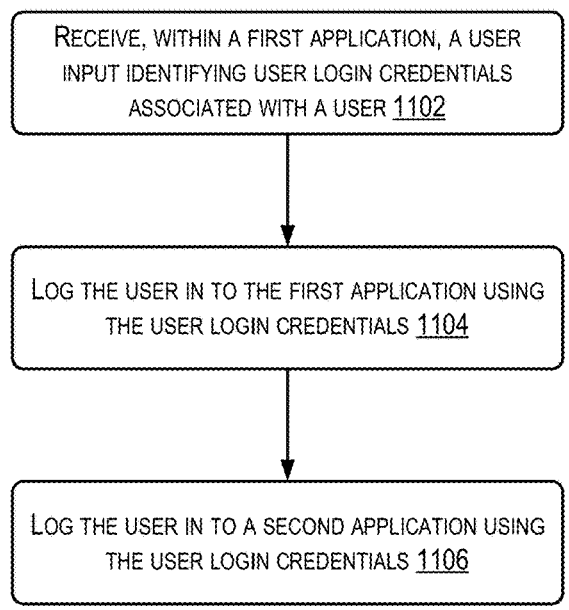
FIG. 11 is another exemplary flowchart illustrating the process including example acts or techniques relating to bi-directional application switching while maintaining contextual information.

FIG. 11 illustrates the process 1100 including example acts or techniques relating to bi-directional application switching while maintaining contextual information, according to at least one example. The switching engine 106 within the application switching service 102 and/or the switching module 114 within an application 112 of the user device 104 performs the process 1100 of FIG. 11.

The process 1100 begins at 1102 by receiving, within a first application, a user input identifying user login credentials associated with a user. The first application can run on a mobile device. In some examples, the first application may maintain an association with other applications for which the user login credentials can be used for logging in. The user login credentials can include a username and password. In some examples, the username and password are specific to the first application or shared among more than one application including the first application.

At 1104, the process 1100 includes logging the user in to the first application using the user login credentials. In some examples, at least a portion of the user login credentials is encrypted.

At 1106, the process 1100 includes logging the user in to a second application of the mobile device using the user login credentials. This logging in may occur without further user input and/or without presenting additional information at a display of the mobile device. In this manner, the logging in can occur in the background. In some examples, the logging in occurs in a manner that at least informs the user that the logging in is occurring or has happened. For example, some information associated with the second application can be presented at the display. In some examples, the process 1100 further includes, shifting back to the first application after logging the user in to the second application, which can occur with or without the user taking notice.

Figure 12:
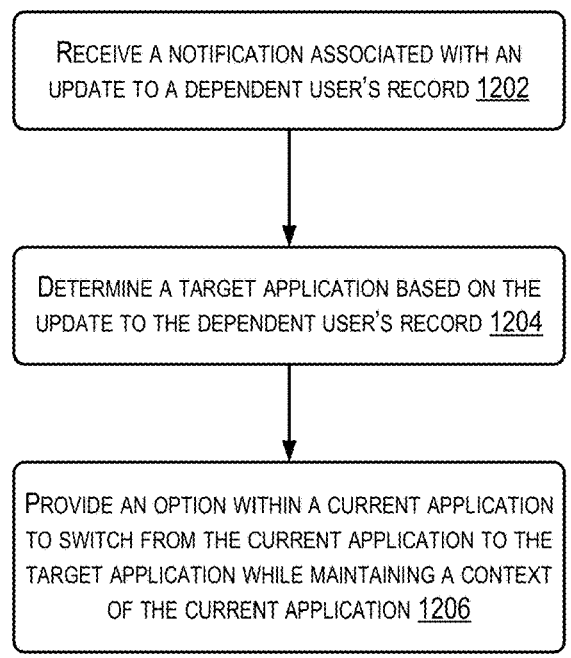
FIG. 12 is another exemplary flowchart illustrating the process including example acts or techniques relating to bi-directional application switching while maintaining contextual information.

FIG. 12 illustrates the process 1200 including example acts or techniques relating to bi-directional application switching while maintaining contextual information, according to at least one example. The switching engine 106 within the application switching service 102 and/or the switching module 114 within an application 112 of the user device 104 performs the process 1200 of FIG. 12.

The process 1200 begins at 1202 by receiving a notification associated with an update to a dependent user record. The dependent user record is associated with a dependent user. The notification is received at a mobile device. The notification can be received with a current application open on the mobile device and while presenting information associated with the dependent user. For example, the current application can be configured to present information about the dependent user at a first high level of detail.

At 1204, the process 1200 includes determining a target application based on the update to the dependent user record. This can include accessing a table of predefined associations that identifies a set of target applications based on an update to the dependent user record and, in some examples, based on the current application. In some examples, the associations define that the target application is associated with an update type associated with the update.

At 1206, the process 1200 includes providing an option within the current application to switch from the current application to the target application while maintaining a context of the current application. For example, the context of the current application can include an identification the dependent user, an identification of an authorized user using the current application, any data input at the current application relating to the dependent user, and any other information relating to context. To switch from the current application to the target application while maintaining the context of the current application includes interacting with the application switching service to identify the context of the current application and pass it to the target application in a manner that enables the target application to load the context.

Figure 13:
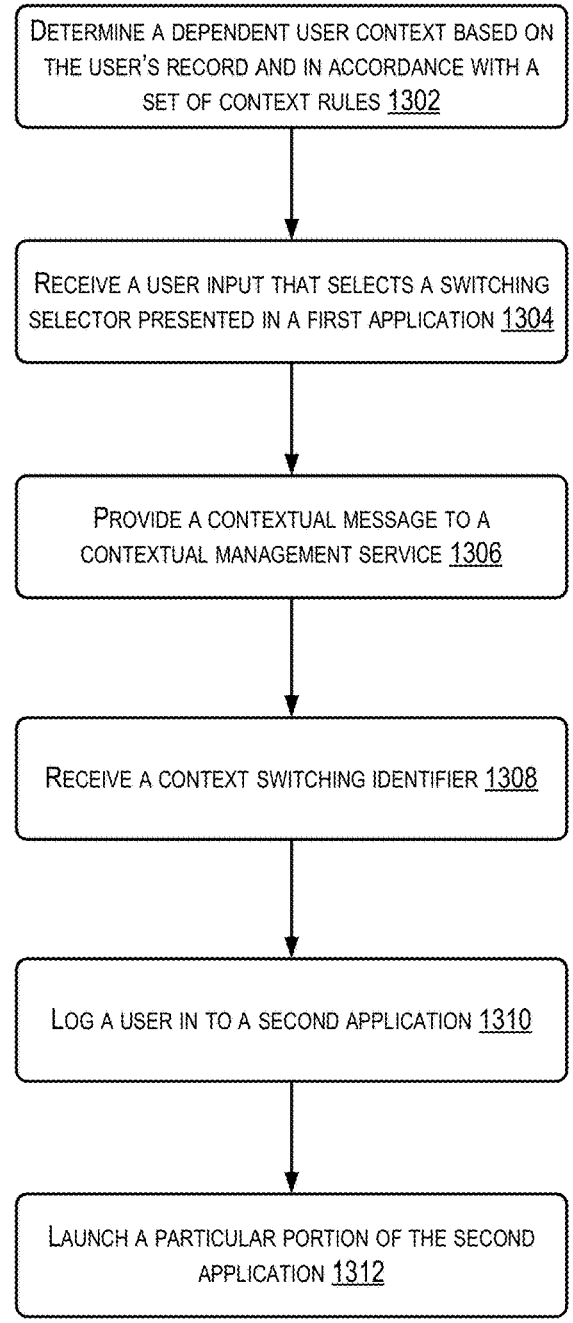
FIG. 13 is another exemplary flowchart illustrating the process including example acts or techniques relating to bi-directional application switching while maintaining contextual information.

FIG. 13 illustrates the process 1300 including example acts or techniques relating to bi-directional application switching while maintaining contextual information, according to at least one example. The switching engine 106 within the application switching service 102 and/or the switching module 114 within an application 112 of the user device 104 performs the process 1300 of FIG. 13.

The process 1300 begins at 1302 by determining a dependent user context based on a dependent user record and in accordance with a set of context rules. The dependent user context is associated with the dependent user. The set of context rules define, given a set of data available at a first application, whether a particular dependent user context exists.

At 1304, the process 1300 includes receiving a user input that selects a switching selector presented in a first application. The first application presents first information associated with the dependent user. The switching selector identifies a second application and is associated with a plurality of contextual parameters. The contextual parameters define what types of contextual data are relevant for switching to the second application.

At 1306, the process 1300 includes providing a contextual request to an application switching service. The request is sent responsive to receiving the user input at 1304. The contextual request at least identifies the plurality of parameters and the dependent user context. In some examples, the contextual request also identifies a plurality of values corresponding to the plurality of parameters. The plurality of values can be obtained by the first application.

At 1308, the process 1300 includes receiving a context switching identifier. The context switching identifier includes a plurality of values corresponding to the plurality of parameters. The plurality of values at least identify the dependent user and user login credentials for a user of the first application and the second application. The context switching identifier can be encrypted. The mobile device can decrypt the context switching identifier and use the data in the context switching identifier to load the second application.

At 1310, the process 1300 includes logging a user in to the second application. This can include using the user login credentials to log in to the second application. The login credentials are stored as value(s) in the plurality of values.

AT 1312, the process 1300 includes launching a particular portion of the second application. This can include causing the second application to display second information associated with the dependent user. Launching the particular portion of the second application is based on a value from the plurality of values.

Figure 14:
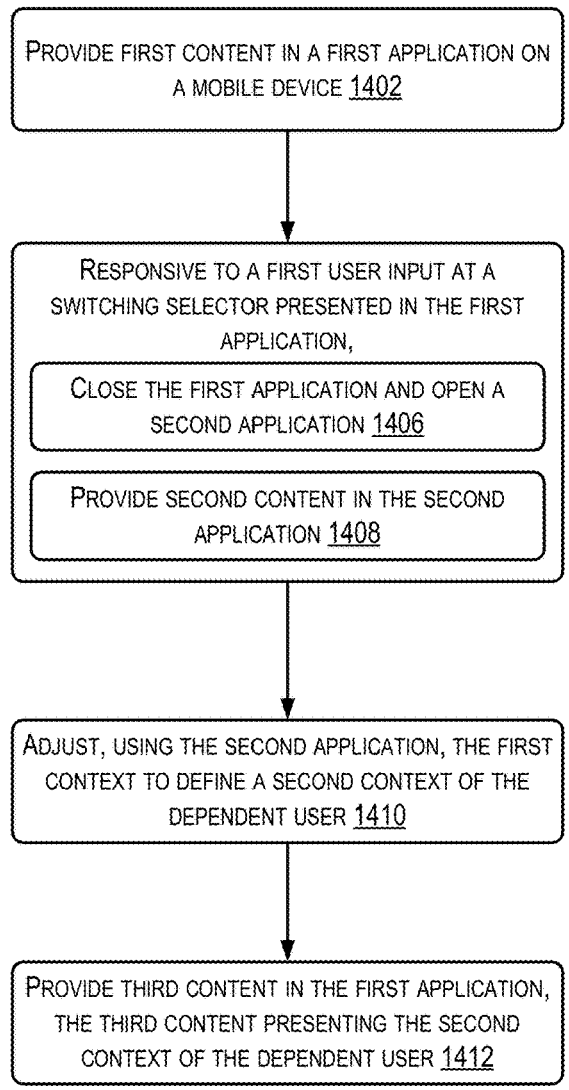
FIG. 14 is another exemplary flowchart illustrating the process including example acts or techniques relating to bi-directional application switching while maintaining contextual information.

FIG. 14 illustrates the process 1400 including example acts or techniques relating to bi-directional application switching while maintaining contextual information, according to at least one example. The switching engine 106 within the application switching service 102 and/or the switching module 114 within an application 112 of the user device 104 performs the process 1400 of FIG. 14.

The process 1400 begins at 1402 by providing first content in a first application on a mobile device. The first application is associated with an authorized user. The first content represents a first context of a dependent user At 1406, the process 1400 includes, responsive to a first user input at a switching selector, presented in the first application, closing the first application and opening a second application on the mobile device. The second application is also associated with the authorized user.

At 1408, the process 1400 includes, responsive to the first user input at the switching selector, presented in the first application, providing second content in the second application. The second content can represent the first context of the dependent user.

At 1410, the process 1400 includes adjusting, using the second application, the first context to define a second context of the dependent user. For example, the second application can be used to search a different record of the dependent user and/or search for a different dependent user altogether.

At 1412, the process 1400 includes providing third content in the first application on the mobile device. The third content represents the second context of the dependent user. Operation 1412 is performed after adjusting the first context.

Specific details are given in the above description to provide a thorough understanding of the embodiments. However, it is understood that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Implementation of the techniques, blocks, steps and means described above may be done in various ways. For example, these techniques, blocks, steps, and means may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments may be described as a process which is depicted as a flowchart, a flow diagram, a swim diagram, a data flow diagram, a structure diagram, or a block diagram. Although a depiction may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, network transmission, etc.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed is:

1. A computer-implemented method, comprising:

determining, by a handheld device and during a current session of a first application, contextual information that defines a patient context, wherein the contextual information is determined according to a set of context rules based on (i) first contextual information comprising a patient record obtained from a first remote system, (ii) second contextual information comprising an alert or an alarm relating to the patient and obtained from a second remote system, (iii) third contextual information comprising provider information associated with a provider that is operating the handheld device and treating the patient, and (iv) fourth contextual information comprising a unique identifier of the first application;

receiving a user input at the handheld device that selects a switching selector presented in the first application during the current session, the first application presenting first information associated with the patient and the patient record, the switching selector identifying a second application;

responsive to receiving the user input, providing, by a handheld device, a contextual request to an application programming interface (API) of an application switching service that is separate from the handheld user device, the contextual request at least identifying the contextual information as a plurality of contextual parameters to customize the second application for the patient and the patient record, wherein the application switching service is a third remote system that is distinct from the first and second remote systems;

receiving, by the handheld user device and from the application switching service, an encrypted uniform resource locator (URL) including a plurality of values corresponding to the plurality of contextual parameters, wherein the URL is generated by the application switching service using the unique identifier of the first application and the plurality of values, the plurality of values at least identifying the (i) patient, (ii) a portion of the contextual information, and (iii) and user login credentials, wherein the user login credentials are for the provider providing health care to the patient based upon information from the patient record;

decrypting, by the handheld device, the encrypted URL to identify the plurality of values; and after decrypting the encrypted URL, loading, by the handheld device, the URL to cause:

logging, by the handheld device, the provider in to the second application using a first value of the plurality of values corresponding to the user login credentials to authorize the provider access to the patient record for the patient for providing health care; and launching, by the handheld device, a particular portion of the second application using a second value of the plurality of values corresponding to the portion of the contextual information to display second information associated with the patient to allow the provider to access the health record according to the portion of the contextual information.

2. The computer-implemented method of claim 1, wherein the set of context rules define actions of the first application and the second application given the patient context.

3. The computer-implemented method of claim 1, wherein the switching selector is a user interface element.

4. The computer-implemented method of claim 1, wherein the plurality of contextual parameters comprise two or more of the patient identifier, a provider identifier, or the user login credentials.

5. The computer-implemented method of claim 1, wherein the particular portion of the second application presents information specific to the patient.

6. The computer-implemented method of claim 1, wherein the user input is provided by the provider who is responsible for providing medical care to the patient.

7. The computer-implemented method of claim 1, wherein the first remote system comprises a first record management endpoint and the second remote system comprises a second record management endpoint.

8. The computer implemented method of claim 1, further comprising presenting, by the handheld device, a notification at the handheld device while the first application is open on the handheld device, the notification (i) identifying the patient, (ii) including an indication of the second information associated with the patient, and (ii) presenting the switching selector for switching from the first application to the second application to view the second information.

9. The computer implemented method of claim 8, wherein receiving the user input at the handheld device that selects the switching selector comprises receiving the user input by selection of the switching selector presented in the notification.

10. A non-transitory computer-readable storage device comprising computer-executable instructions that, when executed by a computer system, cause the computer system to perform operations comprising:

determine, by a handheld device and during a current session of a first application, contextual information that defines a patient context, wherein the contextual information is determined according to a set of context rules based on (i) first contextual information comprising a patient record obtained from a first remote system, (ii) second contextual information comprising an alert or an alarm relating to the patient and obtained from a second remote system, (iii) third contextual information comprising provider information associated with a provider that is operating the handheld device and treating the patient, and (iv) fourth contextual information comprising a unique identifier of the first application;

receive a user input at the handheld device that selects a switching selector presented in the first application during the current session, the first application presenting first information associated with the patient and the patient record, the switching selector identifying a second application;

responsive to receiving the user input, provide, by a handheld device, a contextual request to an application programming interface (API) of an application switching service that is separate from the handheld user device, the contextual request at least identifying the contextual information as a plurality of contextual parameters to customize the second application for the patient and the patient record, wherein the application switching service is a third remote system that is distinct from the first and second remote systems;

receive, by the handheld device and from the application switching service, an encrypted uniform resource locator (URL) including a plurality of values corresponding to the plurality of contextual parameters, wherein the URL is generated by the application switching service using the unique identifier of the first application and the plurality of values, the plurality of values at least identifying (i) the patient, (ii) a portion of the contextual information, and (iii) user login credentials, wherein the user login credentials are for the provider providing health care to the patient based upon information from the patient record;

decrypt, by the handheld device, the encrypted URL to identify the plurality of values; and after decrypting the encrypted URL, load, by the handheld device, the URL to:
 log, by the handheld device, the provider in to the second application using a first value of the plurality of values corresponding to the user login credentials; and
 launch, by the handheld device, a particular portion of the second application using a second value of the plurality of values corresponding to the portion of the contextual information to display second information associated with the patient to allow the provider to access the health record according to the portion of the contextual information.

11. The non-transitory computer-readable storage device of claim 10, wherein the set of context rules define actions of the first application and the second application given the patient context.

12. The non-transitory computer-readable storage device of claim 10, wherein the plurality of contextual parameters comprise two or more of the patient identifier, a provider identifier, or the user login credentials.

13. The non-transitory computer-readable storage device of claim 10, wherein the particular portion of the second application present information specific to the patient.

14. The non-transitory computer-readable storage device of claim 10, wherein the first remote system comprises a first record management endpoint and the second remote system comprises a second record management endpoint.

15. The non-transitory computer-readable storage device of claim 10, wherein the user input is provided by the provider who is responsible for providing medical care to the patient.

16. A handheld device, comprising:
 memory storing computer executable instructions; and
 a processor configured to access the memory and execute the computer-executable instructions to at least:
  determine, by the handheld device and during a current session of a first application, and during a current session of a first application, contextual information that defines a patient context, wherein the contextual information is determined according to a set of context rules based on (i) first contextual information comprising a patient record obtained from a first remote system, (ii) second contextual information comprising an alert or an alarm relating to the patient and obtained from a second remote system, (iii) third contextual information comprising provider information associated with a provider that is operating the handheld device and treating the patient, and (iv) fourth contextual information comprising a unique identifier of the first application;
  receive a user input at the handheld device that selects a switching selector presented in the first application during the current session, the first application presenting first information associated with the patient and the patient record, the switching selector identifying a second application;
  responsive to receiving the user input, provide, by the handheld device, a contextual request to an application programming interface (API) of an application switching service that is separate from the handheld user device, the contextual request at least identifying the contextual information as a plurality of contextual parameters to customize the second application for the patient and the patient record, wherein the application switching service is a third remote system that is distinct from the first and second remote systems;
  receive, by the handheld device and from the application switching service, an encrypted uniform resource locator (URL) including a plurality of values corresponding to the plurality of contextual parameters, wherein the URL is generated by the application switching service using the unique identifier of the first application and the plurality of values, the plurality of values at least identifying (i) the patient, (ii) a portion of the contextual information, and (iii) user login credentials, wherein the user login credentials are for the provider providing health care to the patient based upon information from the patient record;
  decrypt, by the handheld device, the encrypted URL to identify the plurality of values; and
  after decrypting the encrypted URL, load, by the handheld device, the URL to:
   log, by the handheld device, the provider in to the second application using a first value of the plurality of values corresponding to the user login credentials to authorize the provider access to the patient record for the patient for providing health care; and
   launch, by the handheld device, a particular portion of the second application using a second value of the plurality of values corresponding to the portion of the contextual information to display second information associated with the patient to allow the provider to access the health record according to the portion of the contextual information.

17. The computing device of claim 16, wherein the set of context rules define actions of the first application and the second application given the patient context.

18. The computing device of claim 16, wherein the first remote system comprises a first record management endpoint and the second remote system comprises a second record management endpoint.

* * * * *

UNITED STATES PATENT AND TRADEMARK OFFICE
CERTIFICATE OF CORRECTION

PATENT NO. : 11,243,688 B1
APPLICATION NO. : 16/704922
DATED : February 8, 2022
INVENTOR(S) : Ron Remy and Sajikumar Aravind Page 1 of 1

It is certified that error appears in the above-identified patent and that said Letters Patent is hereby corrected as shown below:

In the Claims

Column 17, Line 42, Claim 1: after "handheld" please delete "user".
Column 17, Line 49, Claim 1: after "handheld" please delete "user".
Column 17, Line 57, Claim 1: after "(iii)" please delete "and".
Column 18, Line 8, Claim 1: replace "health" with --patient--.
Column 18, Line 31, Claim 8: replace "computer implemented" with --computer-implemented--.
Column 18, Line 35, Claim 8: after "second" please insert --contextual--.
Column 18, Line 38, Claim 8: after "to view the second" please insert --contextual--.
Column 18, Line 39, Claim 9: replace "computer implemented" with --computer-implemented--.
Column 19, Line 4, Claim 10: after "handheld" please delete "user".
Column 19, Line 36, Claim 10: replace "health" with --patient--.
Column 19, Line 48, Claim 13: replace "present" with --presents--.
Column 19, Line 58, Claim 16: replace "computer executable" with --computer-executable--.
Column 20, Line 21, Claim 16: after "handheld" please delete "user".
Column 20, Line 56, Claim 16: replace "health" with --patient--.
Column 20, Line 59, Claim 17: replace "computing" with --handheld--.
Column 20, Line 62, Claim 18: replace "computing" with --handheld--.

Signed and Sealed this
Nineteenth Day of April, 2022

Katherine Kelly Vidal
*Director of the United States Patent and Trademark Office*